(12) United States Patent
Baldwin et al.

(10) Patent No.: US 6,678,058 B2
(45) Date of Patent: Jan. 13, 2004

(54) INTEGRATED ALIGNMENT AND CALIBRATION OF OPTICAL SYSTEM

(75) Inventors: Leo B. Baldwin, Beaverton, OR (US); Frank G. Evans, Dundee, OR (US)

(73) Assignee: Electro Scientific Industries, Inc., Portland, OR (US)

( * ) Notice: Subject to any disclaimer, the term of this patent is extended or adjusted under 35 U.S.C. 154(b) by 172 days.

(21) Appl. No.: 10/039,249

(22) Filed: Oct. 24, 2001

(65) Prior Publication Data
US 2002/0113970 A1 Aug. 22, 2002

Related U.S. Application Data

(60) Provisional application No. 60/243,165, filed on Oct. 25, 2000.

(51) Int. Cl.⁷ .............................................. G01B 11/24
(52) U.S. Cl. ...................... 356/609; 356/620; 356/401
(58) Field of Search ............................. 356/609, 614, 356/401, 620

(56) References Cited

U.S. PATENT DOCUMENTS

| | | | |
|---|---|---|---|
| 5,257,336 A | 10/1993 | Dautartas | 385/93 |
| 5,298,988 A | 3/1994 | Everett et al. | 348/87 |
| 5,537,204 A | 7/1996 | Woodhouse | 356/243 |
| 6,043,877 A | 3/2000 | Land | 356/243.1 |
| 6,055,055 A | 4/2000 | Toh | 356/376 |

Primary Examiner—Frank G. Font
Assistant Examiner—Layla Lauchman
(74) Attorney, Agent, or Firm—Young & Basile P.C.

(57) ABSTRACT

A calibration system within an optical inspection apparatus comprising a sensor, lens, fiducials, and a CPU. The CPU is configured to receive information from the sensor relating to the fiducial coordinate system and the sensor coordinate system, and the fiducials are used to determine a physical relationship between the sensor coordinates and fiducial coordinates. The calibration system has a means for calibrating the inspection system and measuring critical dimensions of an object in an accurate manner on-the-fly without additional set-up or manual calibration of the system.

20 Claims, 4 Drawing Sheets

INTEGRATED ALIGNMENT AND CALIBRATION OF OPTICAL SYSTEM

This application claims benefit of provisional app. No. 60/243,165 filed Oct. 25, 2000.

FIELD OF THE INVENTION

The present invention relates to the calibration of optical instruments for high precision machine vision inspection applications.

BACKGROUND OF THE INVENTION

In industrial deployment of robotic systems, there is in general a need to precisely determine the position of an object, typically a workpiece or semiconductor, so that the robotic system can align the workpiece with a second object, for instance, to a mating workpiece or to a tool. In certain applications, for example, the fabrication and testing of microelectronic circuits, this alignment must be performed with extreme precision, for example, to less than 1 micron ($1 \times 10^{-6}$ meters). In these circumstances, an external alignment system is generally required. Typically, such a system is an optical, non-contact system known in the art as a machine vision system and, more specifically, as a machine vision alignment system.

In general, the alignment system will consist of a light source to illuminate the object if it is not self luminous, and a sensor to sense the emitted or reflected light. The captured information is either presented to a human operator or automatically analyzed by an associated processor.

In certain applications, there may be two (or more) such systems, with one system viewing the workpiece, and one viewing the tool. In general, each system will include appropriate light sources to illuminate each object, lens to focus the images, and sensors. Each system will typically be connected to a single processor and/or a single monitor. In practice, each system may be combined, in whole or in part, into one assembly to conserve space or cost, or both, so long as the combined assembly is still able to adequately view the workpiece and the tool either simultaneously or in turn.

In operation, the object, or certain features of the object apparent to the sensing system are detected, and their location determined relative to the sensing system. These features are known in the art as fiducial marks or fiducials. Fiducials may be defined by pre-existing features on the object or may be defined by marks artificially placed on the object.

The sensor may be a focal plane array sensor (for example a CCD sensor or a CMOS sensor) comprised of a array of picture elements (known in the art as pixels) and associated imaging optics. The location of the object, or the location of a fiducial on the object, may be determined as a function of the pixel location on the sensor. The location may be defined by a first number of pixels or fractional pixels from a first edge of the senor, and a second number of pixels or fractional pixels from a second edge of the sensor, the second edge being non-parallel to the first edge and, in general, orthogonal to the first edge.

It is well known in the art that for such a system to have merit, it is necessary to relate the measured parameters in image space, for example, a position measured by the pixel location on the sensor, to parameters in object, or real world space, for example, in millimeters at the workpiece or millimeters at the tool. The parameters in object space may be used, for example, to guide the robotically manipulated tool. It is understood that the object coordinates are not necessarily in millimeters and may be based on an artificial measurement scheme which may be native to the robotic system.

In theory, it is possible to create a mathematical transformation between measurements made on the sensor and the object or world coordinates. For example, one could characterize the dimensions of the pixels of the focal plane array sensor, the focal length of a lens, and the image distance and object distance of the system, and the precise location of the sensor and lens relative to the workpiece, and determine an image to object coordinate transformation. However, the errors in characterizing each component of the system will, in general, be cumulative in determining the coordinate transformation of the system.

In practice, it is generally more effective to coordinate the system empirically by measuring a known object with the system, and determine a coordinate transformation that relates the known parameters of the object to the coordinates of the sensing system. With this method, all of the relevant parameters of the alignment system can be determined with one operation. In the art, the known object is called a calibration object if it is substantially three-dimensional in nature, or a calibration fiducial if it is substantially two-dimensional in nature, for example, a mark made on a suitable object.

In the case where two sensing systems are used, the calibration object will present a target which can be viewed by each of the two systems, simultaneously or in turn, and provide a unique point of reference by which the coordinate systems of each system may be correlated to the coordinate systems of the object or objects and to one another. If it is not possible or not convenient to view a single unique target with each system, the calibration object will, in general, consist of two (or more) targets, one for each alignment system. The spatial relationship between the two (or more) targets will be precisely known, so that the coordinate systems of each system can be precisely correlated to one another.

In practice, a device employing a machine vision alignment system will be calibrated when it is first set up. It will be calibrated whenever any component of the system is adjusted or changed, for example, if the lens is changed, zoomed, or refocused. In general, it will be calibrated every time a new job is started. It is also standard practice to recalibrate the system periodically, such as every day or every shift, to correct for mechanical instabilities of the system, or thermally induced deformations. Typically, these calibrations are a non-productive phase of operation.

With reference to FIG. 1, there is shown the current state-of-the-art. The current state-of-the-art involves measuring the position of a calibration fiducial 10 in object or real world coordinates (x,y) with respect to a focal plane array sensor 12 in camera coordinates (p,q), which is considered to be mechanically fixed in place with respect to the imaging optics 14. From the apparent position and size of the calibration fiducial 10, as imaged on the focal plane array sensor 12, the position of the camera and the magnification of the optics are inferred and stored within the computing device 16 portion of the machine vision system. This is possible because the size and position of the fiducial are known in object coordinate system (x,y) of the workpiece 18. These values are used to transform the coordinates of a fiducial 20 on the workpiece 18 as measured on the focal plane array sensor 12 in camera coordinate (p,q) to object coordinate (x,y) in space of the workpiece 18. This operation, (p,q)→(x,y), is known in the art as the image to world coordinate transformation.

If additional alignment systems are deployed, a similar operation may be performed on the additional focal plane array sensor(s) 22 and imaging optics 24 to measure the position of a fiducial 26 on a second object, for example, a robotic tool 28.

Several patents refine this basic technique, including several that deal with calibration issues. For example, Woodhouse (U.S. Pat. No. 5,537,204) shows a workpiece being temporarily replaced with a chrome-on-glass fiducial target for the purpose of calibration. Dautartas (U.S. Pat. No. 5,257,336) shows placement of fiducials directly on the workpiece for the purpose of alignment and, in particular, the workpiece being a light emitting diode package and the tool holding an optical fiber to be aligned with the light emitting diode. Everett (U.S. Pat. No. 5,298,988) shows a virtual image of a fiducial optically projected to a point in space in place of a physical fiducial for calibration purposes.

All of these references consider the alignment system to be a separate closed system, for which calibration is performed externally. This approach requires the alignment system to be physically stable; a requirement which, in general, precludes any of the internal components from moving between the calibration phase of operation and measurement phase of operation, for such a movement would introduce a random error in the accuracy of the alignment unless the motion of the element in question is extremely precise.

Since precise motion control generally requires substantial additional volume, mass and cost to achieve, standard practice is to make any adjustments to the system prior to calibration, and to lock all of the adjustment mechanisms to prevent unintended variations after calibration. This permits the use of relatively imprecise mechanisms or manual adjustments. Examples of where the adjustment mechanisms would be employed include adjusting optical elements for variations in object distance or magnification or light transfer efficiency; known respectively in the art as focus, zoom, and aperture.

A need has arisen to improve the calibration process in machine vision.

SUMMARY OF THE INVENTION

The present invention provides for a calibration system positioned within an optical inspection apparatus. The apparatus includes a sensor, a lens defining a focal plane external to the optical inspection apparatus. The lens is operative to focus an image of an object onto the sensor. At least two calibration fiducials are located internally to the optical inspection apparatus. The fiducials are positioned adjacent to the focal plane of the lens and are used to calibrate the sensor.

A second embodiment includes a partially reflective member that separates the reflected illuminating rays and directs the rays toward a plurality of objects, thereby making a plurality of objects visible to the inspection system. A fiducial internal to the apparatus is used with the sensing system and the optical system as a calibration standard for inspecting and simultaneously measuring a plurality of objects.

DESCRIPTION OF THE PREFERRED EMBODIMENTS

The present invention provides for "on-the-fly" calibration of a machine vision system. In particular, the present invention provides for a calibration fiducial positioned within the vision system itself, thereby eliminating the need for a separate calibration fiducial. By placing a calibration fiducial within the vision system itself, the vision system can be calibrated at any time and does not require the system to be shut down to calibrate.

Figure 1:
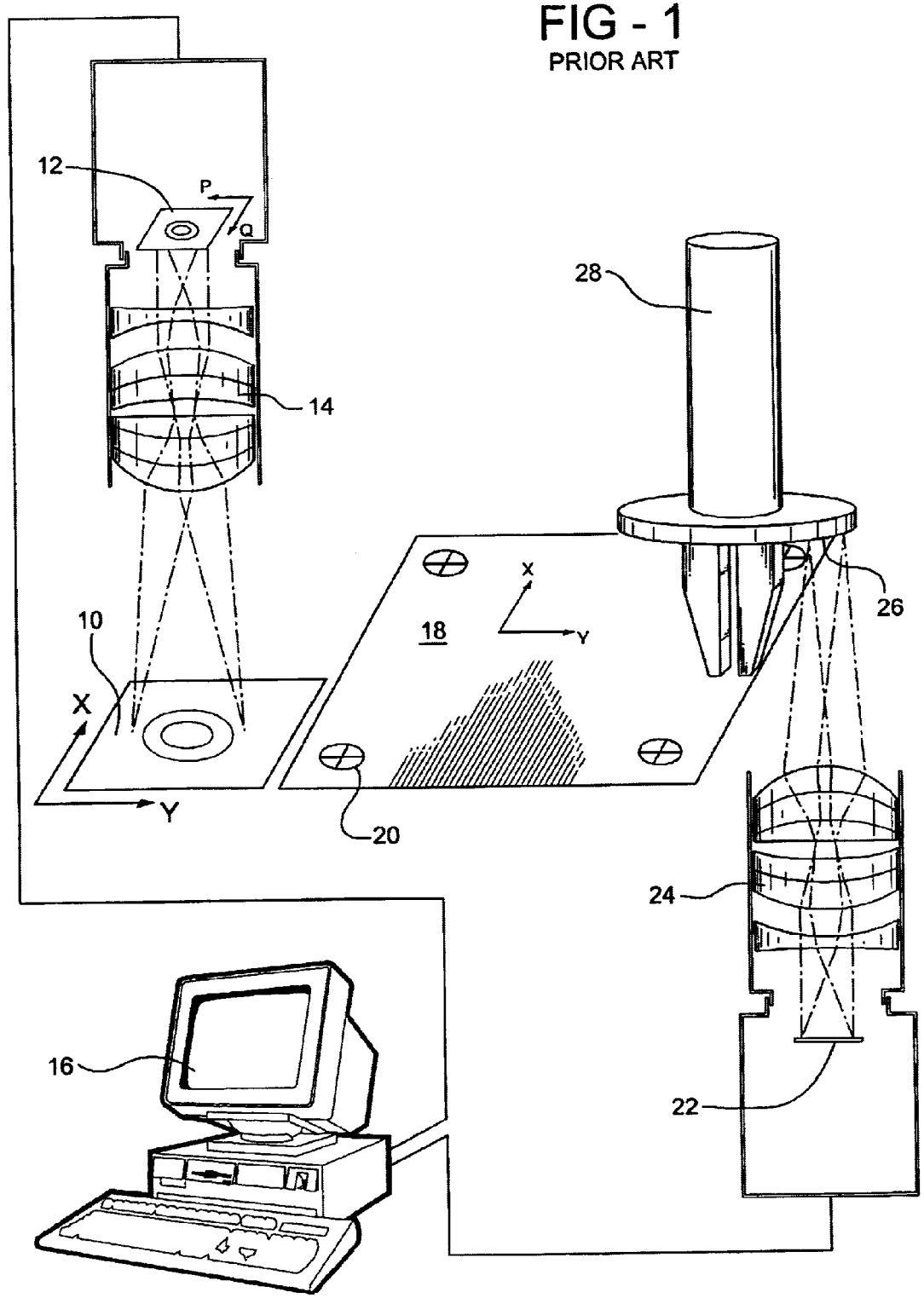
FIG. 1 is a schematic representation of an inspection and calibration system of the prior art.
Figure 2:
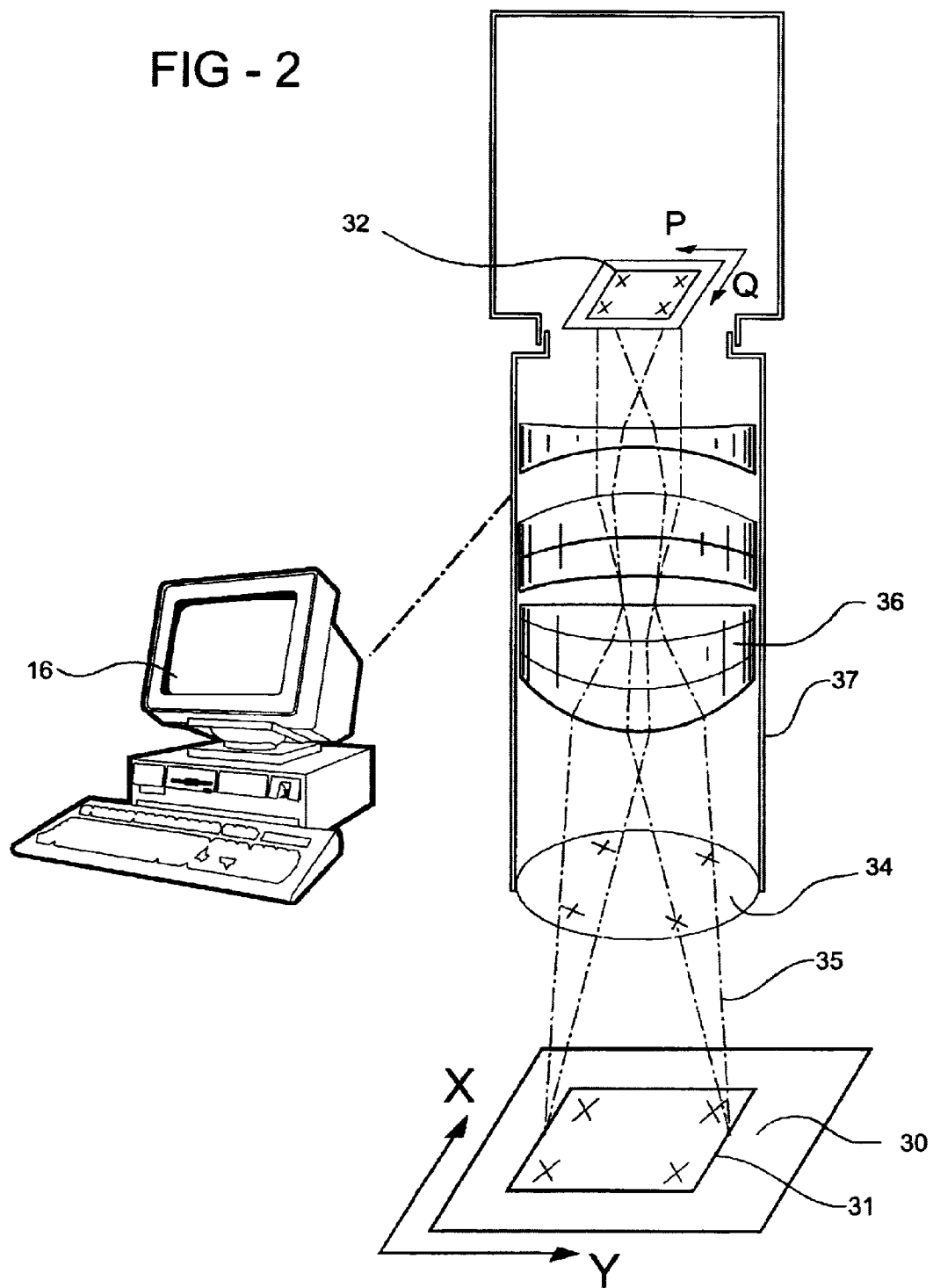
FIG. 2 is a schematic representation of an inspection and calibration system according to a first aspect of the present invention.

With reference to the figures, wherein like elements are numbered alike, the preferred embodiments of the present invention are shown. With reference to FIG. 2, there is shown a first preferred embodiment of the present invention. The present invention adds a calibration fiducial element 34 between the imaging optics 36 and the object plane 30. One of the objectives of the present invention to allow for perturbations within the electro-optical portion of the alignment system without a significant loss of overall system precision and accuracy. The perturbations may be a result of external influences such as vibration or thermal deformations, or of a deliberate action such as adjusting the optical elements of the system to gain a different focus or magnification.

An accurate coordinate transformation function (p,q)→(x,y) is determined between the object coordinates (x,y) and the sensing system 32 coordinates (p,q). This transformation is used to determine the location and orientation of known calibration fiducial 34 associated with the optical system 36 in world coordinates (x,y). In the preferred embodiment, optical system 36 is a telecentric lens which, as illustrated, allows light to enter and exit the lens in a parallel manner. By including additional fiducials 34 within optical system 36, calibrations can be performed at any time. Calibration may be performed at job changes or when changes are made to the system. In addition, because the calibration fiducial 34 is associated with the system, calibration may be performed with very little effect on productivity, including before every alignment operation.

The ability to perform an operation without interrupting production is sometimes referred to in the art as performing an operation on-the-fly. The present invention allows recalibration of the system to be performed on-the-fly. The ability to perform a calibration at any time during operation, including before every alignment, confers many benefits to the machine vision alignment system. Productivity will be improved, as normal operation does not have to be interrupted to perform scheduled recalibrations. The system may operate to the same accuracy over a greater temperature range, as thermal distortions may be compensated for during operation by recalibrating as necessary. Mechanical systems can be made less robust because the system can be continuously calibrated and hence can be manufactured at a lower cost. Prior to the instant invention, the system had to remain stable for a period of time between periodic off-line recalibrations. With on-the-fly calibration, mechanical stability may be required over a shorter time, or it may be irrelevant if the associated fiducials and the object to be aligned are captured within a common image.

In a preferred embodiment, calibration fiducial is disposed between the object 30 and the imaging optics 36, and is supported on a structure 37 common to the imaging optics.

It will be apparent to a person skilled in the art that calibration fiducial 34 will, in general, not be in the exact image plane of the imaging optics 36. The image plane of the lens within the system is generally coplanar with workpiece 31. Reflected light 35 transmits the characteristic image of the workpiece 31 to the sensing system 32. It will also be apparent to a person skilled in the art that calibration fiducial 34 can generally be arranged sufficiently proximate to the image plane 30 that an adequate image will be formed. The adequate image may be out of focus, but it is known to someone skilled in the art that this condition can actually increase the accuracy with which the location of the fiducial features can be determined.

The precise distance of calibration fiducial 34 from the image plane of the optics 36 which will provide an adequate or an optimal image, will depend on several system variables such as focal ratio of the lens and image distance, but can be determined by a person skilled in the art. This distance may also have constraints imposed by other system requirements, such as clearance for robotic motion or out-of-plane features of the workpiece.

In a preferred embodiment, calibration fiducial 34 is designed to provide adequate markings for calibration while, at the same time, minimally occluding the camera's field of view so as not to interfere with the alignment operation.

Figure 3A:
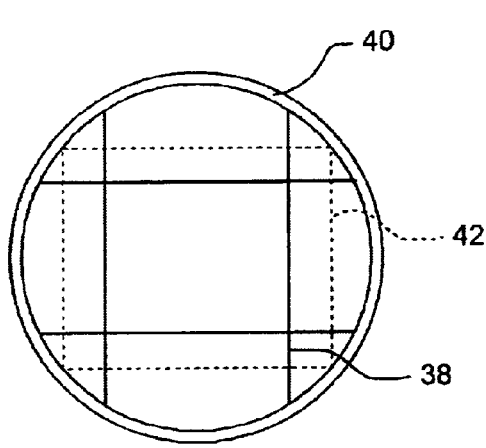
FIG. 3A shows a first preferred embodiment of a calibration fiducial.

With reference to FIGS. 3A through 3E there are shown a plurality of different preferred embodiments of calibration fiducial 34. In FIG. 3A, calibration fiducial 34 includes the intersections of four wires or fibers 38, attached to a suitable mounting frame 40 and arranged so that the wire intersections are placed near the corners of the camera's field of view, indicated by the dashed rectangle 42. The wires are sufficiently thin so that they do not interfere substantially with the alignment operations, and the intersection points uniquely define stable reference points for the "on-the-fly" recalibrations.

Figure 3B:
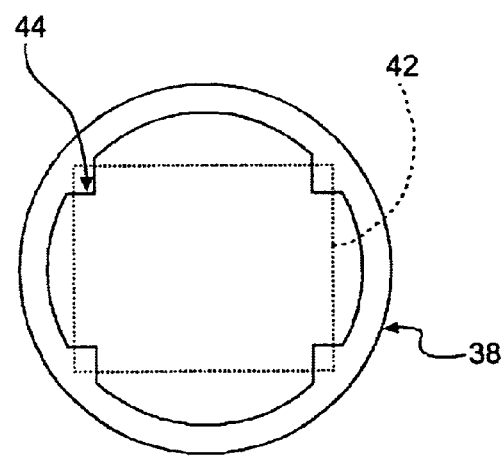
FIG. 3B shows a second preferred embodiment of a calibration fiducial.

In FIG. 3B, a fiducial frame 40 fabricated with an aperture that generally admits the image forming rays without interference, except for protrusions 44 that occlude the camera's 15 field of view in unobtrusive areas such as the corners. FIG. 3B shows four protrusions 44 occluding a small amount of the field of view, indicated by the dashed lined rectangle 42, at the four corners. The protrusions provide the unique reference points for the "on-the-fly" recalibrations.

Figure 3C:
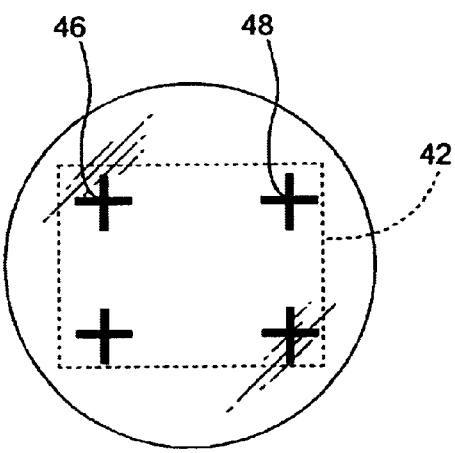
FIG. 3C shows a third preferred embodiment of a calibration fiducial.
Figure 3D:
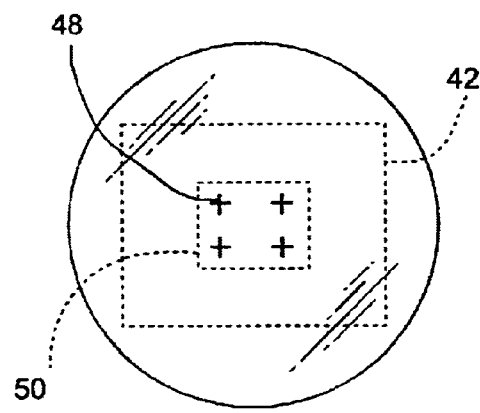
FIG. 3D shows a fourth preferred embodiment of a calibration fiducial.

In a third embodiment, illustrated in FIG. 3C, calibration fiducials 34 include fiducials 46 which are lightly etched onto a transparent element, such as a flat glass disk. This type of fiducial will interfere minimally with the alignment operation.

If an optical system with variable magnification is employed, such as a zoom optical system, there will be a plurality of fields of view. In this case, it may be desirable to place the fiducials such that they are visible when the magnification of the optical system is maximal and the field of view is correspondingly minimal. This situation is shown in another preferred embodiment illustrated in FIG. 3D, whereby four fiducials 48 are disposed to fall within the minimal field of view as indicated by the dashed line rectangle 50. Note that fiducials so disposed also fall within the maximal field of view as indicated by the dashed rectangle 42.

Figure 3E:
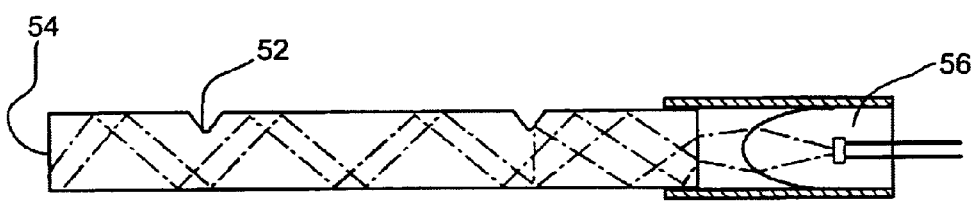
FIG. 3E shows a fifth preferred embodiment of a calibration fiducial.

FIG. 3E illustrates another preferred embodiment of calibration fiducials 34, wherein the fiducials are etched and made luminous. In particular, fiducials 52 are etched into an otherwise polished plano transparent window 54. An appropriate illumination source such as a light emitting diode 56, supplies illumination into the edge of the window. By a process known in the art as light piping by total internal reflection, the light reflects back and forth between the two surfaces of the window and escapes only at fiducials 52. In this way, fiducials 52 can be etched very lightly into the window 50 that they are substantially invisible to the camera when the illumination source is off by virtue of being very small and out of focus. When the illumination source is turned on, the fiducials will be easily visible despite their small size, due to their luminosity. In this way, the fiducials can be made substantially invisible during the alignment phase of the operation and substantially visible during the recalibration phase of operation by controlling the state of the illumination source. In practice, the illumination source would be controlled by the same digital computing means that performs the machine vision alignment functions.

Figure 4:
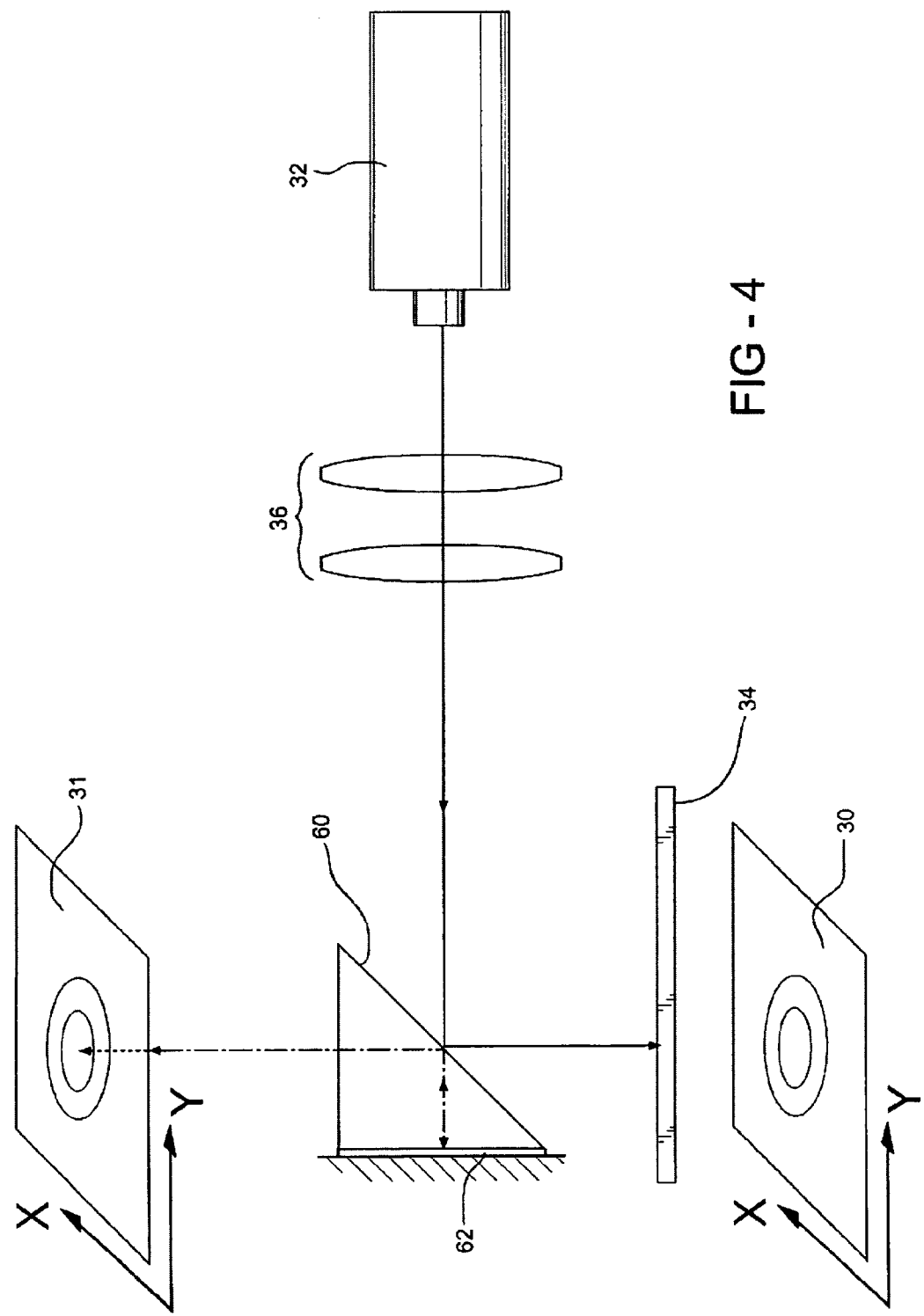
FIG. 4 is a schematic representation of a calibration system according to a second aspect of the present invention.

With reference to FIG. 4, a single calibration fiducial 34 may be used to calibrate a sensor operative to view a plurality of objects. As shown, a full silvered mirror 62 used in combination with a 33% reflective mirror 60, may be positioned between first and second objects 30 and 31 such that light reflected from first and second objects 30 and 31 are directed to sensor 32. In the present embodiment, a calibration fiducial 34 is used to calibrate objects 30 and 31 above and below mirror 62. The sensor 32 and optics 36 are positioned orthogonally from first and second objects 30 and 31. It is understood that the first and second objects may represent a tool and workpiece. In the embodiment illustrated in FIG. 4, the fiducial 34 may be used to calibrate between (x,y) and (p,q) relative the first and second objects 30 and 31.

While the invention has been described in connection with what is presently considered to be the most practical and preferred embodiment, it is to be understood that the invention is not to be limited to the disclosed embodiments but, on the contrary, is intended to cover various modifications and equivalent arrangements.

What is claimed is:

1. A calibration system positioned within an optical inspection apparatus comprising:
   a sensor operative to capture an image of an object;
   a lens defining a focal plane external to the optical inspection apparatus and operative to focus an image of an object onto the sensor, the object being external to the optical inspection apparatus; and
   at least two calibration fiducials located internally to the optical inspection apparatus, the fiducials being positioned adjacent to the focal plane of the lens; wherein the fiducials are operative to calibrate the sensor.

2. The fiducials of claim 1, wherein the fiducials comprise a plurality of wires.

3. The fiducials of claim 2, wherein the wires are mounted to the optical inspection apparatus using a common frame.

4. The calibration system of claim 1, further comprising a transparent member positioned adjacent to the focal plane of the lens, and the calibration fiducials comprise etchings on the transparent member.

5. The calibration system of claim 1, wherein the transparent member has a light source such that when the light illuminates the transparent member, the calibration fiducials are illuminated.

6. A calibration system as in claim 1, wherein the lens is a telecentric lens.

7. The calibration system of claim 1, wherein a zoom lens operates to bring the fiducials into and out of focus.

8. The calibration system of claim 1, further comprising a mounting frame attached to the optical inspection apparatus that encompasses a sensing system's field of view, and the calibration fiducials are defined by a plurality of wires attached to the perimeter of the mounting frame, so as to form wire crossings wherein the crossings are shown in the field of view for use as fiducials.

9. The calibration system of claim 1, wherein a means for calibrating the inspection system is provided for measuring critical dimensions of the object in an accurate manner and on-the-fly without additional setup and/or manual calibration of the apparatus by a human operator.

10. The calibration system of claim 1, wherein the apparatus further comprises:
   a means to transfer the measurements to a central processing unit (CPU) for storage, mathematical manipulation, and subsequent recall;
   the CPU is configured to receive information from the sensor relating the fiducial coordinate system to the sensor coordinate system; and
   the fiducials configured to determine a relationship between a sensor dimension and a fiducial dimension.

11. The calibration system of claim 1, wherein the apparatus further comprises:
   a fixture to place and to hold the workpiece in proper position for measurement of critical dimensions.

12. The calibration system of claim 1, wherein the fiducial elements are used to correct for reduced accuracy of the calibration system caused by thermal and mechanical deformations of the apparatus.

13. The calibration system of claim 1, wherein a window with the fiducial elements affixed is used as a means to protect the apparatus' imaging optics from external environmental damage.

14. A calibrating system for an optical inspection apparatus comprising:
   a sensor operative to capture an image of an object;
   a lens defining a focal plane external to the optical inspection apparatus and operative to focus an image of an object onto the sensor; the object being external to the optical inspection apparatus;
   at least two fiducials located internally to the optical inspection apparatus, the fiducials being positioned adjacent to the focal plane of the lens; wherein the fiducials are operative to calibrate the sensor; and
   a partially reflective member operative to allow the sensor to capture images of a plurality of objects.

15. The fiducials of claim 14, wherein the fiducials comprise a plurality of wires.

16. The calibration system of claim 14, further comprising a transparent member positioned adjacent to the focal plane of the lens, and the calibration fiducials comprise etchings on the transparent member.

17. The calibration system of claim 14, wherein the transparent member has a light source such that when the light illuminates the transparent member, the calibration fiducials are illuminated.

18. The calibration system of claim 14, further comprising a mounting frame attached to the optical inspection apparatus that encompasses a sensing system's field of view, and the calibration fiducials are defined by a plurality of wires attached to the perimeter of the mounting frame, so as to form wire crossings wherein the crossings are shown in the field of view for use as fiducials.

19. The calibration system of claim 14, wherein a means for calibrating the inspection system is provided for measuring critical dimensions of the object in an accurate manner and on-the-fly without additional setup and/or manual calibration of the apparatus by a human operator.

20. The calibration system of claim 14, wherein the apparatus further comprises:
   a means to transfer the measurements to a central processing unit (CPU) for storage, mathematical manipulation, and subsequent recall;
   the CPU is configured to receive information from the sensor relating the fiducial coordinate system to the sensor coordinate system; and
   the fiducials configured to determine a relationship between a sensor dimension and a fiducial dimension.

* * * * *